(12) United States Patent
Al-Majnouni et al.

(10) Patent No.: US 11,807,816 B2
(45) Date of Patent: Nov. 7, 2023

(54) PROCESS INTEGRATION FOR CRACKING LIGHT PARAFFINIC HYDROCARBONS

(71) Applicant: SABIC Global Technologies B.V., Bergen op Zoom (NL)

(72) Inventors: Khalid A. Al-Majnouni, Riyadh (SA); Nabil Al-Yassir, Riyadh (SA); Naif Aldalaan, Riyadh (SA); Ahmed Al-Zenaidi, Riyadh (SA); Khalid Almusaiteer, Thuwal (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/467,121

(22) PCT Filed: Dec. 13, 2017

(86) PCT No.: PCT/IB2017/057913
§ 371 (c)(1),
(2) Date: Jun. 6, 2019

(87) PCT Pub. No.: WO2018/116085
PCT Pub. Date: Jun. 28, 2018

(65) Prior Publication Data
US 2019/0316042 A1    Oct. 17, 2019

Related U.S. Application Data

(60) Provisional application No. 62/436,163, filed on Dec. 19, 2016.

(51) Int. Cl.
*C07C 4/06*      (2006.01)
*C10G 11/18*     (2006.01)

(52) U.S. Cl.
CPC ............. *C10G 11/182* (2013.01); *C07C 4/06* (2013.01); *C07C 2529/08* (2013.01);
(Continued)

(58) Field of Classification Search
CPC ................. C10G 11/18; C10G 11/182; C10G 2300/1044; C10G 2300/4093;
(Continued)

(56) References Cited

U.S. PATENT DOCUMENTS 4,422,925 A    12/1983  Williams et al. .............. 208/75
4,541,922 A     9/1985  Lomas et al. ................ 208/164
(Continued)

FOREIGN PATENT DOCUMENTS

CN    1274342 A    11/2000
CN    1708573 A    12/2005
(Continued)

OTHER PUBLICATIONS

And Mochizuki et al. (Applied Catalysis A: General 449 (2012) 188-197) (Year: 2012).*
(Continued)

*Primary Examiner* — In Suk C Bullock
*Assistant Examiner* — Jason Y Chong
(74) *Attorney, Agent, or Firm* — Norton Rose Fulbright US LLP

(57) ABSTRACT

Systems and methods for the catalytic cracking of light hydrocarbons, such as naphtha, to form light olefins and aromatics is disclosed. The systems and methods may include a catalytic cracking process that involves mixing catalyst with a gas and then this mixture is used to contact a hydrocarbon feed, e.g., light straight run naphtha or heavy straight run naphtha. The hydrocarbon feed may be mixed with dry gas such as methane and/or hydrogen to dilute the hydrocarbon feed, before the hydrocarbon feed is contacted with the catalyst/gas mixture.

13 Claims, 4 Drawing Sheets

(52) U.S. Cl.
CPC .. *C07C 2529/40* (2013.01); *C10G 2300/1044* (2013.01); *C10G 2300/4093* (2013.01); *C10G 2300/708* (2013.01); *C10G 2400/20* (2013.01)

(58) Field of Classification Search
CPC .......... C10G 2300/708; C10G 2400/20; C07C 4/06; C07C 2529/08; C07C 2529/40; Y02P 30/40
See application file for complete search history.

(56) References Cited

U.S. PATENT DOCUMENTS

| | | | | |
|---|---|---|---|---|
| 4,541,923 | A | | 9/1985 | Lomas et al. .................. 208/164 |
| 4,830,728 | A | | 5/1989 | Herbst et al. .................... 208/78 |
| 5,264,115 | A | * | 11/1993 | Mauleon ................ C10G 11/18 208/113 |
| 5,348,642 | A | * | 9/1994 | Serrand .................. C10G 11/18 208/113 |
| 6,184,167 | B1 | * | 2/2001 | Van Mao ................ B01J 29/40 502/63 |
| 6,548,725 | B2 | | 4/2003 | Froment et al. .............. 585/653 |
| 7,670,478 | B2 | * | 3/2010 | Swan, III ................ B01J 4/002 208/113 |
| 8,293,961 | B2 | | 10/2012 | Choi et al. .................... 585/651 |
| 2002/0005375 | A1 | * | 1/2002 | Schlosser ................ C10G 11/18 208/113 |
| 2006/0144758 | A1 | | 7/2006 | Swan et al. |
| 2008/0314799 | A1 | * | 12/2008 | Li ............................ C07C 4/06 208/118 |
| 2009/0124842 | A1 | * | 5/2009 | Reagan ................. C10G 11/05 585/653 |
| 2009/0288985 | A1 | * | 11/2009 | Long ...................... C10G 11/18 208/57 |
| 2010/0158767 | A1 | * | 6/2010 | Mehlberg ............... C10G 11/18 422/145 |
| 2016/0333280 | A1 | | 11/2016 | Subramani et al. |
| 2019/0330539 | A1 | * | 10/2019 | Al-Majnouni ........... B01J 29/06 |

FOREIGN PATENT DOCUMENTS

| | | |
|---|---|---|
| CN | 101293806 A | 10/2008 |
| CN | 100465250 C | 3/2009 |
| CN | 100554229 C | 10/2009 |
| CN | 102337148 A | 2/2012 |
| EP | 2660288 A1 | 11/2013 |
| WO | WO2010053482 A1 | 5/2010 |
| WO | WO2013016660 A1 | 1/2013 |
| WO | WO2016137955 A1 | 9/2016 |

OTHER PUBLICATIONS

Kubo et al. (Microporous and Mesoporous Materials 188 (2014) 23-29) (Year: 2014).*
International Search Report and Written Opinion from PCT/IB2017/057913 dated Mar. 19, 2018, 9 pages.
Yamaguchi et al. "Deactivation of ZSM-5 zeolite during catalytic steam cracking of n-hexane." Fuel Processing Technology, 126 (2014) 343-349.
Xiao, Chouclian. "Organic Chemistry", p. 38, Sun Yat-sen University Press, Jan. 2000, English Translation, 4 pages.
Chen et al. "The Process and Engineering of Catalytic Cracking." China Petrochemical Press, 1995, pp. 847-848. English Translation Provided.

* cited by examiner

PROCESS INTEGRATION FOR CRACKING LIGHT PARAFFINIC HYDROCARBONS

CROSS REFERENCE TO RELATED APPLICATIONS

This application is a national phase application under 35 U.S.C. § 371 of International Application No. PCT/IB2017/057913 filed Dec. 13, 2017, which claims priority to U.S. Provisional Patent Application No. 62/436,163 filed Dec. 19, 2016. The entire contents of each of the above-referenced disclosures is specifically incorporated by reference herein without disclaimer.

FIELD OF INVENTION

The present invention generally relates to the production of light olefins. More specifically, the present invention relates to the catalytic cracking of light hydrocarbons, such as naphtha, to form light olefins and aromatics.

BACKGROUND OF THE INVENTION

Distilling crude oil to produce products such as butane (or lighter hydrocarbons), straight run gasoline, naphtha, kerosene, light gas oil, heavy gas oil, and straight run residue is simply separating the crude oil into its various constituents. Thus, under set processing conditions, the relative proportions of the products produced from a particular type of crude oil will roughly remain constant. However, based on market demands, it may be more economical to be able to increase the proportion of one or more of the products at the expense of other products. For example, when the demand for gasoline is high, it may be more economical to produce more gasoline than heavy gas oil. Thus, processes have been developed to convert one type of distilled product to another. One such process is catalytic cracking, where longer and heavier hydrocarbon molecules are contacted with a catalyst at high temperatures and pressures to break them into lighter and shorter hydrocarbon molecules.

Catalytic cracking often involves converting naphtha, gas oils, and straight run residue to high octane gasoline, light fuels, and light olefins. Typically, a liquid oil stream is contacted with a catalyst, in a reactor, under a certain temperature and pressure to cause the oil to crack and produce lighter products. As the cracking reaction occurs, coke, a carbonaceous material, is formed and deposits on the catalyst. As a result of the coke deposits on the catalyst, the catalyst becomes less effective or inactive—that is, the catalyst becomes spent. The spent catalyst is sent to a regenerator where the coke is removed from the catalyst by combusting the coke. The regenerated catalyst is then returned to the reactor.

When the catalytic cracking process is employed to crack a mixture of light hydrocarbons such as light naphtha and heavy naphtha to produce light olefins and aromatics, the cracking catalyst is typically a zeolite based catalyst. The zeolite catalyst is exposed at high temperature (above 490° C.) to the hydrocarbon feed, which is mixed with steam. The hydrocarbon feed is mixed with the steam for a number of reasons. For example, the steam (1) dilutes the reactant so as to reduce the hydrocarbon partial pressure, (2) atomizes the feed in the case of vacuum gas oil, and (3) improves fluidization. In addition, steam is an inexpensive raw material. Mixing steam with the hydrocarbon feed, however, has its drawbacks. For example, the steam deactivates the catalyst by dealumination, causing structural damage and acidity reduction. Therefore, catalyst activity reduces with time. Consequently, make up catalyst has to be added to the process daily to maintain the catalyst activity at equilibrium level. In short, the presence of steam at high temperature causes catalyst deactivation.

To minimize catalyst dealumination, the zeolite is impregnated with phosphorous. The phosphorous interacts with the Bronsted acid sites in zeolite forming monomer or cationic pyrophosphate that partially neutralizes the Bronsted acid sites. Thus hydrothermal stability is enhanced. Phosphorus addition has not been successful in reducing dealumination of the catalyst. The catalyst deactivation problem becomes severe if steam is present when the reaction temperature is increased above 550° C., as is the case when cracking paraffinic feedstock.

One type of catalytic cracking process involves the conversion of paraffinic hydrocarbons having boiling point less than 350° C. into light olefins ($C_2$ to $C_4$ olefins). However, carrying out this conversion with high selectively and high yields poses a challenge from both process configuration and catalyst design standpoints. The conversion of paraffinic hydrocarbons having boiling point less than 350° C. into light olefins requires high temperature (above 600° C.) and relatively short residence time to overcome the endothermicity of the reactions and prevent oligomerization of the light olefins.

One commercial process for converting naphtha feed into light olefins was developed by KBR. The technology is called Advanced Catalytic Olefins (ACO™) and is based on a fluid catalytic cracking process where catalysts are circulated between reactor and regenerator. In this process, steam is used to improve catalyst fluidization and reduce the partial pressure of the reactive hydrocarbon.

BRIEF SUMMARY OF THE INVENTION

A method has been discovered for catalytically cracking hydrocarbon mixtures into light olefins. In embodiments of the invention, the catalyst used in the catalytic cracking process is a solid and is mixed with a gas (fluidizing solid catalyst particles) and then this mixture is used to contact a hydrocarbon feed, e.g., light straight run naphtha or heavy straight run naphtha. Further, in embodiments of the invention, instead of using steam as a diluent, as conventional cracking methods do, the hydrocarbon feed may be mixed with methane to dilute the hydrocarbon feed, before the hydrocarbon feed is contacted with the gas/catalyst mixture (fluidized solid catalyst). In embodiments of the invention, the hydrocarbon mixture that is cracked includes components with a boiling point of less than 350° C.

Embodiments of the invention include a method of producing olefins. The method may include preheating a hydrocarbon feed comprising $C_5$ to $C_7$ hydrocarbons to at least a temperature of 400° C. The method may further include mixing a catalyst with a gas to form a gas/catalyst mixture. After forming the gas/catalyst mixture, the method may further include contacting the gas/catalyst mixture with the preheated hydrocarbon feed comprising $C_5$ to $C_7$ hydrocarbons at reaction conditions sufficient to produce light olefins ($C_2$ to $C_4$ olefins).

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, twenty embodiments are now described. Embodiment 1 is a method of producing olefins, the method including the steps of preheating a hydrocarbon feed including the steps of $C_5$ to $C_7$ hydrocarbons to at least a temperature of 400° C.; mixing a catalyst with a gas to form a gas/catalyst mixture; after forming the gas/catalyst mixture, contacting the gas/catalyst mixture with the preheated hydrocarbon feed including the steps of $C_5$ to $C_7$ hydrocarbons at reaction conditions sufficient to produce light olefins ($C_2$ to $C_4$ olefins). Embodiment 2 is the method of embodiment 1, further including the step of mixing hydrocarbon feedstock with methane ($CH_4$) and/or hydrogen ($H_2$) to dilute the hydrocarbon feedstock and form the hydrocarbon feed. Embodiment 3 is the method of any of embodiments 1 and 2, wherein the gas contains methane ($CH_4$) and/or hydrogen ($H_2$). Embodiment 4 is the method of any of embodiments 1 to 3, wherein the reaction conditions includes a temperature in a range of 500 to 750° C. and pressure in a range of 0.5 to 5 bars. Embodiment 5 is the method of any of embodiments 1 to 4, wherein the mixing occurs at a first point in a riser of a fluid catalytic cracking reactor and the method further includes the steps of allowing the gas/catalyst mixture to rise to a second point in the riser; and injecting the preheated hydrocarbon feed including the steps of $C_5$ to $C_7$ hydrocarbons at the second point in the riser, wherein the contacting the gas/catalyst mixture with the preheated hydrocarbon feed causes cracking of at least some of the $C_5$ to $C_7$ hydrocarbons to produce the light olefins. Embodiment 6 is the method of embodiment 5, wherein the residence time in the fluid catalytic cracking reactor is in a range 1 to 10 seconds. Embodiment 7 is the method of any of embodiments 5 and 6, further including the steps of after the cracking, separating the catalyst from vapors in the fluid catalytic cracking reactor; and sending the catalyst to a catalyst regeneration system for regenerating the catalyst by burning off coke formed on the catalyst during the cracking. Embodiment 8 is the method of embodiment 7, wherein the vapors contain unreacted hydrocarbons of the hydrocarbon feed, the $C_2$ to $C_4$ olefins, and the gas. Embodiment 9 is the method of any of embodiments 7 and 8, further including the steps of after regeneration of the catalyst in the catalyst regeneration system, mixing the regenerated catalyst with additional gas to form a regenerated catalyst/gas mixture; and contact the regenerated catalyst/gas mixture with additional hydrocarbon feed in the riser. Embodiment 10 is the method of any of embodiments 7 to 9 further including the steps of separating the vapors in a downstream separation process to produce at least a product stream including the steps of ethylene, a product stream including the steps of propylene, a product stream including the steps of dry gas. Embodiment 11 is the method of any of embodiments 5 to 10, further including the steps of recycling a $C_4$ to $C_5$ stream of fluid catalytic cracking reactor effluent to mix with the hydrocarbon feed to the fluid catalytic cracking reactor. Embodiment 12 is the method of any of embodiments 1 to 11 wherein the catalyst contains a solid acid based zeolite catalyst selected from the list consisting of: one or more medium pore zeolites, including ZSM-5 and modified ZSM-5; one or more large pore zeolites, including zeolite Y and ultra-stable zeolite Y; and combinations thereof. Embodiment 13 is the method of embodiment 12, wherein the zeolite catalyst is modified by a selection from the list consisting of: dealumination, desilication, chemical treatment, and steaming. Embodiment 14 is the method of any of embodiments 1 to 13, wherein the catalyst is hydrothermally stabilized by impregnation with phosphorous or rare earth metal. Embodiment 15 is the method of any of embodiments 1 to 14, wherein the hydrocarbon feed further contains: one or more of N—$C_5$, I—$C_5$, cycl-$C_5$, N—$C_6$, I—$C_6$, cycl-$C_6$, Benzene, or $C_7$. Embodiment 16 is the method of any of embodiments 1 to 15, wherein the hydrocarbon feed contains light naphtha and/or hydrocarbons that are heavier than $C_5$ to $C_7$ hydrocarbons and that have a boiling point less than 350° C. Embodiment 17 is the method of any of embodiments 1 to 16, wherein the weight ratio of catalyst to hydrocarbon feed is in the range: from 3 to 50 and preferably from 5 to 40. Embodiment 18 is the method of any of embodiments 1 to 17, wherein the gas/hydrocarbon feed weight ratio is in a range 0.1 to 100. Embodiment 19 is the method of any of embodiments 5 to 18, wherein effluent from the fluid catalytic cracking reactor contains methane, ethane, ethylene and propylene, or LPG ($C_3+C_4$). Embodiment 20 is the method of any of embodiments 1 to 19, wherein the hydrocarbon feed is not mixed with steam as part of the method.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for catalytically cracking hydrocarbon mixtures into light olefins. In embodiments of the invention, the catalyst used in the catalytic cracking process is a solid and is mixed with a gas (fluidizing solid catalyst particles) and then this mixture is used to contact a hydrocarbon feed, e.g., light straight run naphtha or heavy straight run naphtha. Further, in embodiments of the invention, instead of using steam as a diluent, as conventional cracking methods do, the hydrocarbon feed may be mixed with methane to dilute the hydrocarbon feed, before the hydrocarbon feed is contacted with the gas/catalyst mixture (fluidized solid catalyst). In embodiments of the invention, the hydrocarbon mixture that is cracked includes components with a boiling point of less than 350° C.

Embodiments of the invention involve a catalytic cracking process that uses dry gas (e.g., methane and/or hydrogen) to dilute the hydrocarbon feed and to fluidize the catalyst. The catalytic cracking may be implemented in a vertical fluid catalytic cracking reactor. According to embodiments of the invention, the dry gas is mixed with the solid catalyst particles and the gas/catalyst mixture (fluidized solid catalyst) formed is fed into a riser of the vertical fluid catalytic cracking reactor at a location upstream and below the hydrocarbon feed entrance into the riser. Thus, in embodiments of the invention, the hydrocarbon feed enters the riser at an elevated location relative the catalyst entrance and meets an upwardly flowing gas/catalyst mixture. In embodiments of the invention, spent catalyst is removed from the reactor, regenerated and returned to the reactor.

Figure 1:
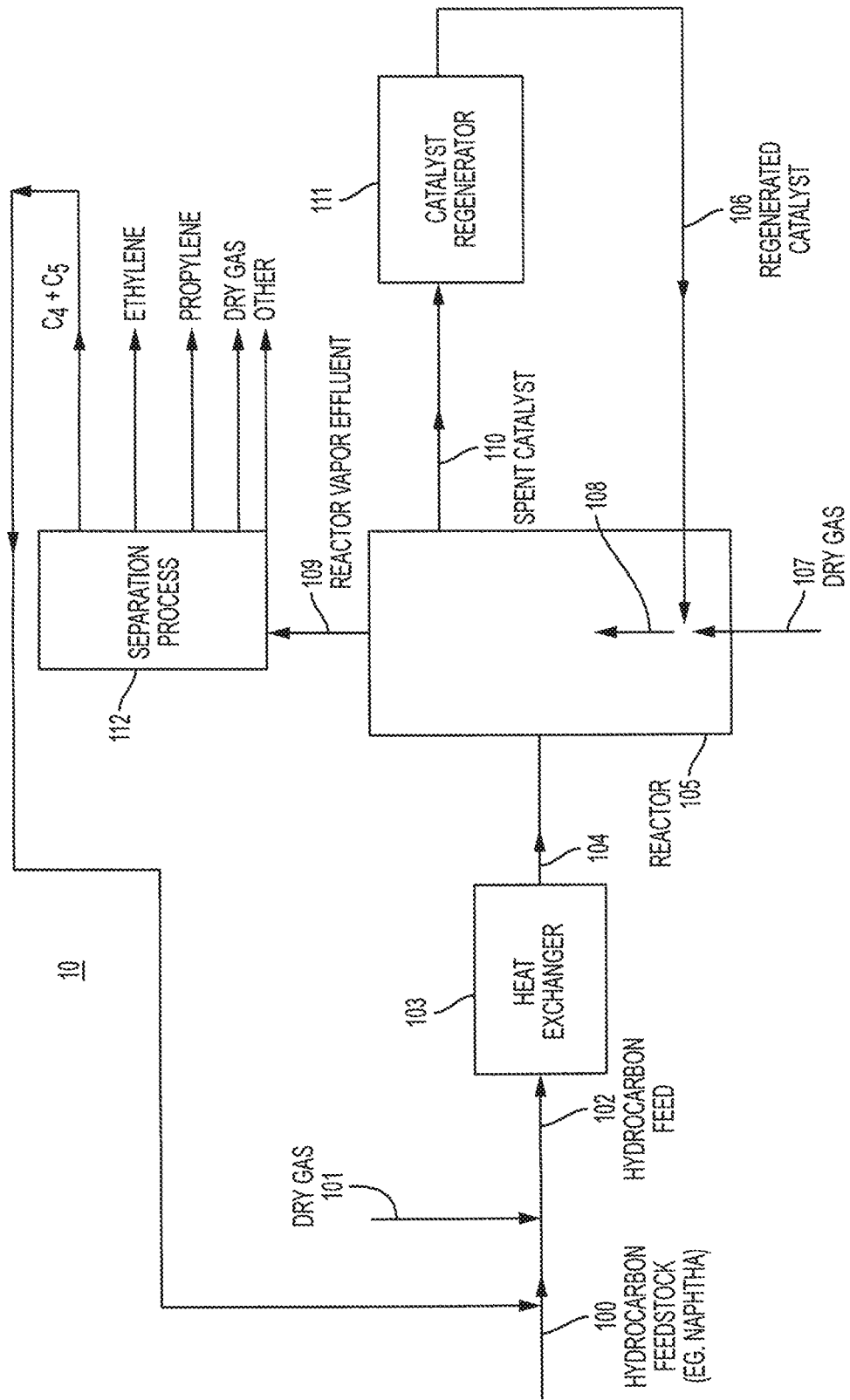
FIG. 1 shows a schematic of a system for cracking a hydrocarbon feedstock to form light olefins, according to embodiments of the invention.
Figure 2:
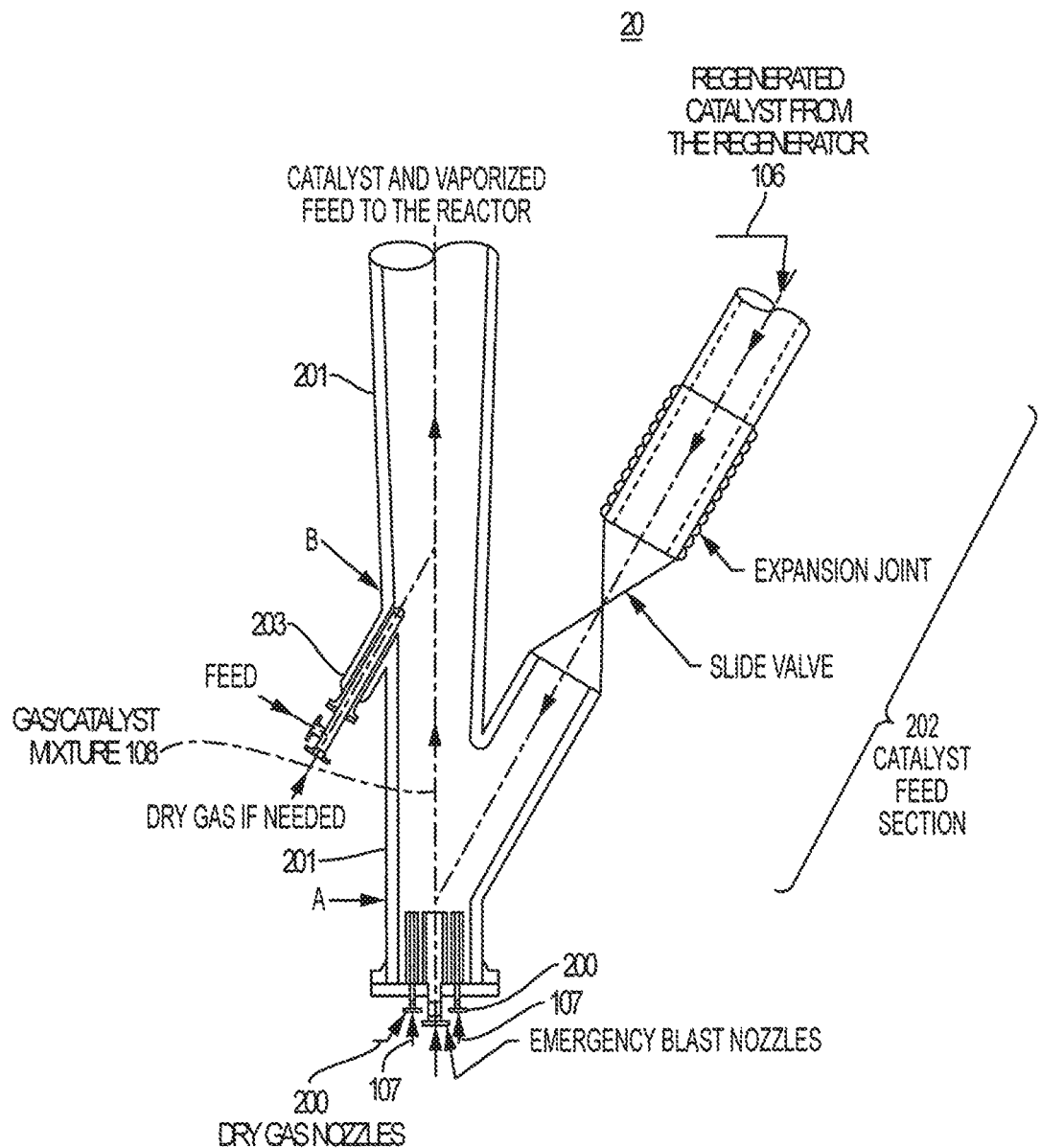
FIG. 2 shows a vertical fluid catalytic cracking riser reactor for cracking a hydrocarbon feedstock to form light olefins, according to embodiments of the invention.
Figure 3:
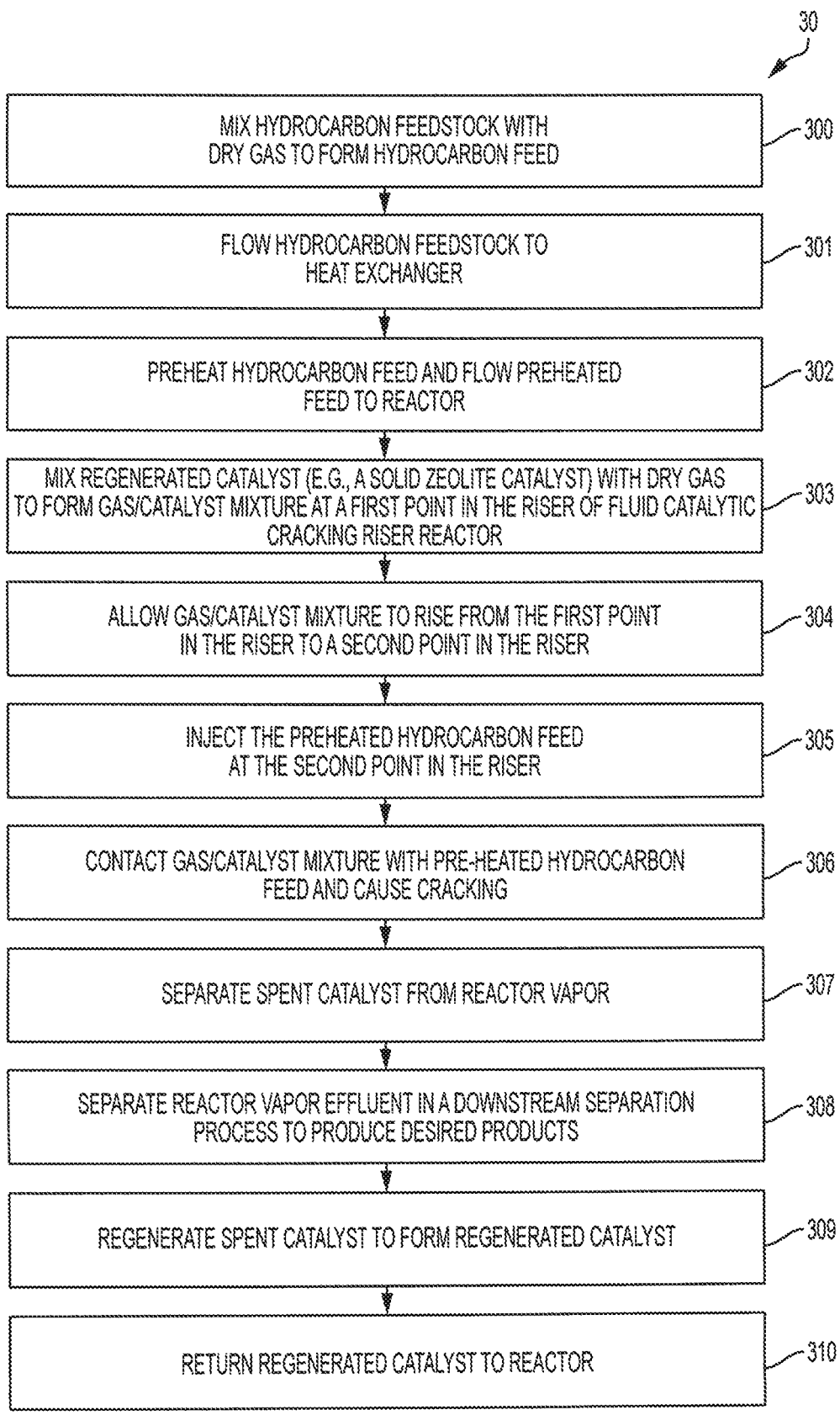
FIG. 3 shows a method for cracking a hydrocarbon feedstock to form light olefins, according to embodiments of the invention.

FIG. 1 shows system 10 for cracking a hydrocarbon feedstock to form light olefins, according to embodiments of the invention. FIG. 2 shows vertical fluid catalytic cracking riser reactor 20 for cracking a hydrocarbon feedstock, according to embodiments of the invention. Vertical fluid catalytic cracking riser reactor 20 may be used as a reactor in system 10. FIG. 3 shows method 30 for cracking a hydrocarbon feedstock, according to embodiments of the invention. Method 30 may be implemented, at least in part, by system 10 and/or vertical fluid catalytic cracking riser reactor 20.

FIG. 3 shows that method 30 may begin at block 300, which may involve, with respect to system 10 as shown in FIG. 1, mixing hydrocarbon feedstock 100 with dry gas 101 to form hydrocarbon feed 102. Hydrocarbon feedstock 100 may include a mixture of hydrocarbons having a boiling point less than 350° C. For example, hydrocarbon feedstock 100 may include light naphtha having $C_5$ to $C_7$ hydrocarbons and/or heavier hydrocarbon with boiling point of less than 350° C. In embodiments of the invention, hydrocarbon feedstock 100 may include one or more of N—$C_5$, I—$C_5$, cycl-$C_5$, N—$C_6$, I—$C_6$, cycl-$C_6$, hydrocarbons, benzene, or $C_7$ hydrocarbons. Dry gas 101 may include methane ($CH_4$) and/or hydrogen ($H_2$).

Mixing hydrocarbon feedstock 100 with dry gas 101 dilutes hydrocarbon feedstock 100 so that, in embodiments of the invention, the dry gas/feed weight ratio in hydrocarbon feed 102 is 0.1 to 100 to reduce the hydrocarbon partial pressure and to ensure proper fluidization flow. When dry gas 101 dilutes hydrocarbon feedstock 100 and thereby reduces the partial pressure of the reactive hydrocarbons in hydrocarbon feed 102, in the cracking process, this reduction in partial pressure reduces side reactions and minimizes catalyst dealumination.

Figure 4:
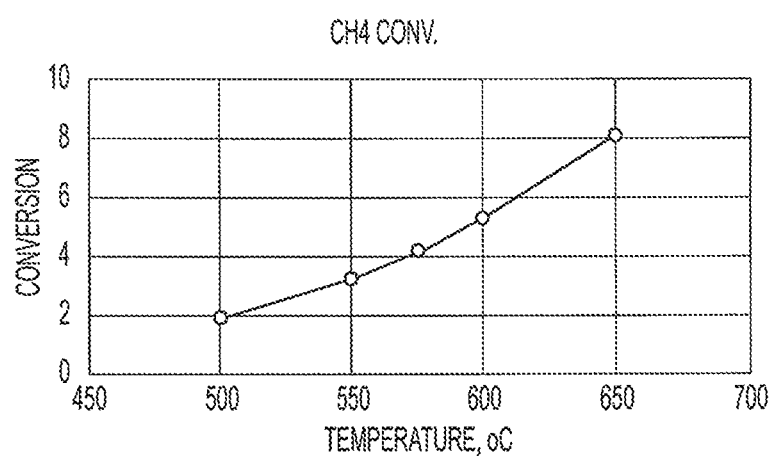
FIG. 4 shows a graph of methane equilibrium conversion as a function of temperature.

As noted above, methane and/or hydrogen are examples of diluents that may be used in embodiments of the invention. Methane is a very stable molecule that has very limited reactivity at the reaction temperature of the catalytic cracking process described herein. FIG. 4 shows a graph of methane equilibrium conversion as a function of temperature. As the graph of FIG. 4 shows, a temperature of 650° C. is required for the equilibrium conversion of methane to reach only 8%. Given the expected residence time in vertical fluid catalytic cracking riser reactor 20, which would be very low, the conversion of methane will be less than the equilibrium conversion. Therefore, methane is reasonably considered as a diluent in the catalytic cracking process described herein to dilute and reduce the partial pressure of the reactive hydrocarbons.

After mixing to form hydrocarbon feed 102 or otherwise providing hydrocarbon feed 102, method 30 may include, at block 301, with respect to system 10 as shown in FIG. 1, flowing hydrocarbon feed 102 to heat exchanger 103. And at block 302, according to embodiments of the invention, heat exchanger 103 preheats hydrocarbon feed 102 to, for example, a temperature in the range from 400° C. to 600° C. to form preheated hydrocarbon feed 104. This temperature, in embodiments of the invention, may be effective in minimizing thermal cracking. Block 302 further includes flowing preheated hydrocarbon feed to reactor 105, as shown in FIG. 1.

Reactor 105 of FIG. 1 is adapted to carry out the catalytic cracking of preheated hydrocarbon feed 104 to form light olefins ($C_2$-$C_4$ olefins). In embodiments of the invention, reactor 105 contacts preheated hydrocarbon feed 104 with regenerated catalyst 106 and dry gas 107 under reaction conditions sufficient to form the light olefins.

In embodiments of the invention, reactor 105 is a riser reactor such as vertical fluid catalytic cracking riser reactor 20, as shown in FIG. 1. FIG. 2 shows vertical fluid catalytic cracking riser reactor 20 may include dry gas nozzles 200 for injecting dry gas, e.g., dry gas 107 (FIG. 1), into riser 201 at lower point A of riser 201. Vertical fluid catalytic cracking riser reactor 20 may also include catalyst feed section 202. Catalyst feed section 202 is in fluid communication with riser 201, as shown in FIG. 2, in a manner so that catalyst (e.g., regenerated catalyst 106, FIG. 1) flows down towards dry gas nozzles 200, while dry gas nozzles 200 are injecting dry gas 107 (FIG. 1) into riser 201. The effect of this is that dry gas 107 flowing upwards is mixed with regenerated catalyst 106 flowing tangentially into the path of dry gas 107 to form a catalyst gas/mixture (fluidized solid catalyst) such as gas/catalyst mixture 108 (FIG. 1).

Vertical fluid catalytic cracking riser reactor 20 may have, at point B, feed injector 203, which leads into riser 201 and is adapted to inject hydrocarbon feed, e.g., preheated hydrocarbon feed 104 (FIG. 1), into riser 201, at point B. Point B is at a higher elevation than point A of vertical fluid catalytic cracking riser reactor 20. Thus, after entering riser 201 at point B, in embodiments of the invention, preheated hydrocarbon feed 104 meets and mixes with rising gas/catalyst mixture 108. In this way, vertical fluid catalytic cracking riser reactor 20 is adapted to contact gas/catalyst mixture 108 with preheated hydrocarbon feed 104.

As can be seen from the discussion above, vertical fluid catalytic cracking riser reactor 20 is adapted to and may be used to carry out aspects of method 30. For example, at block 303, method 30, with respect to system 10 of FIG. 1, may involve mixing regenerated catalyst 106 (e.g., a solid zeolite catalyst) with dry gas comprising methane ($CH_4$) and/or hydrogen ($H_2$) to form gas/catalyst mixture 108 at a first point in a riser of a fluid catalytic cracking riser reactor. In embodiments of the invention, the catalyst to oil weight ratio as a result of this mixing in the reactor is in the range from 3 to 50, and preferably from 5 to 40.

Block 304 involves, with respect to system 10 as shown in FIG. 1, allowing gas/catalyst mixture 108 to rise from a first point in reactor 105 (e.g., point A in the riser of vertical fluid catalytic cracking riser reactor 20) to a second point in reactor 105 (e.g., point B in the riser of vertical fluid catalytic cracking riser reactor 20). According to embodiments of the invention, as gas/catalyst mixture 108 rises, block 305 involves injecting the preheated hydrocarbon feed of block 302 at point B in the riser of vertical fluid catalytic cracking riser reactor 20. In embodiments of the invention, the hydrocarbon feed comprises $C_5$ to $C_7$ hydrocarbons. In this way, block 306 of method 30 may be implemented, which includes contacting gas/catalyst mixture 108 with preheated hydrocarbon feed 104 to cause cracking of at least some of the $C_5$ to $C_7$ hydrocarbons to produce the light olefins.

In embodiments of the invention, one or more of the following may also be produced in reactor 105 (e.g., vertical fluid catalytic cracking riser reactor 20): methane, ethane, ethylene and propylene, or LPG ($C_3+C_4$). The contacting of gas/catalyst mixture 108 with preheated hydrocarbon feed 104 (which may include $C_5$ to $C_7$ hydrocarbons) may be at reaction conditions reaction conditions that include a temperature in a range of 500 to 750° C. and pressure in a range of 0.5 to 5 bars. In embodiments of the invention, the residence time in the fluid catalytic cracking is in a range 1 to 10 seconds.

In embodiments of the invention, reactor 105 (e.g., vertical fluid catalytic cracking riser reactor 20) in normal operation, in method 30, is free from steam. For example, in embodiments of the invention, unlike other conventional catalytic cracking processes, steam is not mixed with the hydrogen feed (not used as a diluent) and the amount of water present in the feed to vertical fluid catalytic cracking riser reactor 20 is zero or substantially zero. In embodiments of the invention, only hydrogen and/or methane is used as diluent of the hydrocarbon feed.

After the cracking process of block 306, method 30 may involve separating contents of reactor 105 (e.g., vertical fluid catalytic cracking riser reactor 20) into spent catalyst 110 and reactor vapor effluent 109, at block 307. Reactor vapor effluent 109 may include unreacted hydrocarbon feed, $C_2$ to $C_4$ olefins, dry gas 101, and dry gas 107. To recover desired products, block 308 may include, with respect to system 10 of FIG. 1, separating reactor vapor effluent 109 in downstream separation process 112 to produce desired products such as a product stream including ethylene, a product stream including propylene, a product stream including dry gas, and a product stream including other products. The other products may be, for example, unreacted hydrocarbons such as $C_4$ to $C_5$ hydrocarbons, which may be recycled and mixed with hydrocarbon feedstock 100, hydrocarbon feed 102, or preheated hydrocarbon feed 104, or combinations thereof, for sending to reactor 105 for further conversion to light olefins, as shown in FIG. 1.

In embodiments of the invention, method 30 may further include, in system 10 as shown in FIG. 1, sending spent catalyst 110 to catalyst regeneration system 111 for regenerating spent catalyst 110 by burning off coke formed on spent catalyst 110 during the cracking process of block 306. Thus, block 309 may involve, in system 10 as shown in FIG. 1, catalyst regeneration system 111 regenerating spent catalyst 110 to form regenerated catalyst 106, which, in embodiments of the invention, is returned to reactor 105, at block 310 of method 30.

Catalysts that may be used for the catalytic cracking process, in embodiments of the invention, include a solid acid based catalyst selected from the list consisting of: one or more spray dried medium pore zeolites, including ZSM-5 and modified ZSM-5; one or more large pore zeolites, including zeolite Y and ultra-stable zeolite Y; and combinations thereof. The zeolite may be modified by demetalization such as dealumination or desilication, chemical treatment and steaming. Further, the catalyst may be hydrothermally stabilized by adding phosphorus or rare earth metal to enhance its thermal stability.

EXAMPLES

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example 1

Cracking of Light Naphtha

In Example 1, a catalyst was tested for light naphtha cracking using a fluidized bed reactor without using steam. The catalyst/feed ratio was 12/1 by weight. Inert gas was used to represent (imitate) the use of methane. In this example, fresh catalyst was used and the conversion rate achieved was 64 wt. %. Table 1 shows the composition of the light naphtha feed in wt. %.

TABLE 1

| (Light Naphtha Feed Composition) Feed (LSRN) | |
|---|---|
| N-C5 | 28.8 |
| I-C5 | 11.8 |
| Cycl-C5 | 1.9 |
| N-C6 | 24.5 |
| I-C6 | 26.9 |
| Cycl-C6 | 4.6 |
| Benzene | 1.3 |
| C7 | 0.3 |
| sum | 100 |

The product distribution as a result of the catalytic cracking of Example 1 is shown in Table 2.

TABLE 2

(Light Naphtha Cracking Over Fluidized Reactors Using Fresh Catalyst)
Fresh Catalytst

| Component | YIELDS, wt % |
| --- | --- |
| Methane | 6.6 |
| Ethane | 8.07 |
| Ethylene + Propylene | 33 |
| LPG (C3 + C4) | 6.23 |
| C4 Olefins | 8.24 |
| heavy product | 37.33 |

Example 2

Comparative Example—Light Naphtha Cracking Over Fluidized Reactors Using Steamed Catalyst In Example 2, fresh catalyst was first steamed at 750° C. outside the reactor to represent (imitate) the steaming effect when steam is mixed with hydrocarbon feed. The steamed catalyst was mixed with equilibrium catalyst. The reaction is conducted in a fluidized bed reactor. The conversion is 56 wt. % and the product distribution is shown in Table 3.

TABLE 3

(Light Naphtha cracking over fluidized reactors using steamed catalyst)
90% Steamed Catalyst + 10% Ecat

| Component | YIELDS, wt % |
| --- | --- |
| Methane | 5.19 |
| Ethane | 5.87 |
| Ethylene + Propylene | 29.98 |
| LPG (C3 + C4) | 5.14 |
| C4 Olefins | 8.23 |
| heavy product | 45.01 |

Example 3

Published Example of n-Hexane Steam Catalytic Cracking

Example 3 was not carried out by the present inventors; rather, Example 3 is a summary of a publication by Aritomo Yamaguchi et. al., Fuel Processing Technology 126 (2014) 343-349. This publication reported on a study of n-hexane steam catalytic cracking. Yamaguchi et. al. showed that catalyst is deactivated steadily from 100% conversion to 53% over five hours. After the catalyst regeneration under oxidative atmosphere, the initial conversion could not pass 66% indicating that catalyst deactivation by dealumination took place.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing olefins, the method comprising:
preheating a hydrocarbon feed comprising $C_5$ to $C_7$ hydrocarbons to at least a temperature of 400° C. to form a preheated hydrocarbon feed;
mixing a catalyst with a gas comprising at least one member selected from the group consisting of methane and hydrogen to form a gas/catalyst mixture;
contacting the gas/catalyst mixture with the preheated hydrocarbon feed at reaction conditions sufficient to produce $C_2$ to $C_4$ olefins; and
mixing a hydrocarbon feedstock with a dry gas member selected from the group consisting of methane and hydrogen to dilute the hydrocarbon feedstock and form the hydrocarbon feed;
wherein the hydrocarbon feedstock is one member selected from the group consisting of light straight run naphtha and heavy straight run naphtha;
wherein the catalyst comprises a solid acid based zeolite catalyst selected from the group consisting of one or more medium pore zeolites, one or more large pore zeolites and combinations thereof;
wherein the zeolite catalyst is only modified by at least one member selected from the group consisting of desilication and steaming;
wherein the reaction conditions comprise a temperature in a range of 500 to 750° C. and pressure in a range of 0.5 to 5 bars;
wherein a weight ratio of dry gas/hydrocarbon feedstock in the hydrocarbon feed ranges from 20 to 100; and
wherein the catalyst is fresh.

2. The method of claim 1, wherein the weight ratio of dry gas/hydrocarbon feedstock in the hydrocarbon feed ranges from 30 to 100.

3. The method of claim 1, wherein the weight ratio of dry gas/hydrocarbon feedstock in the hydrocarbon feed ranges from 50 to 100.

4. The method of claim 1, wherein the zeolite catalyst is modified by desilication.

5. The method of claim 1, wherein the mixing occurs at a first point in a riser of a fluid catalytic cracking reactor and the method further comprises:
allowing the gas/catalyst mixture to rise to a second point in the riser; and
injecting the preheated hydrocarbon feed comprising C5 to C7 hydrocarbons at the second point in the riser, wherein the contacting the gas/catalyst mixture with the preheated hydrocarbon feed causes cracking of at least some of the C5 to C7 hydrocarbons to produce the light olefins, wherein effluent from the fluid catalytic cracking reactor comprises methane, ethane, ethylene and propylene, or LPG($C_3$+$C_4$).

6. The method of claim 1, wherein the mixing occurs at a first point in a riser of a vertical fluid catalytic cracking reactor and the method further comprises:
allowing the gas/catalyst mixture to rise to a second point in the riser; and
injecting the preheated hydrocarbon feed comprising C5 to C7 hydrocarbons at the second point in the riser, wherein the contacting the gas/catalyst mixture with the preheated hydrocarbon feed causes cracking of at least some of the C5 to C7 hydrocarbons to produce the light olefins; and wherein the preheated hydrocarbon feed enters the riser at an elevated location relative the catalyst entrance and meets an upwardly flowing gas/catalyst mixture.

7. The method of claim 1, wherein the catalyst is fresh.

8. The method of claim 1, wherein the zeolite catalyst is modified by steaming.

9. A method of producing olefins, the method comprising:

preheating a hydrocarbon feed comprising $C_5$ to $C_7$ hydrocarbons to at least a temperature of 400° C. to form a preheated hydrocarbon feed;

mixing a catalyst with a gas comprising at least one member selected from the group consisting of methane and hydrogen to form a gas/catalyst mixture;

contacting the gas/catalyst mixture with the preheated hydrocarbon feed at reaction conditions sufficient to produce $C_2$ to $C_4$ olefins;

and mixing a hydrocarbon feedstock with a dry gas selected from the group consisting of methane and hydrogen to dilute the hydrocarbon feedstock and form the hydrocarbon feed;

wherein a weight ratio of dry gas/hydrocarbon feedstock in the hydrocarbon feed is 100; and wherein the catalyst is fresh.

10. The method of claim 9, wherein the hydrocarbon feedstock comprises light straight run naphtha and heavy straight run naphtha.

11. The method of claim 9, wherein the mixing and contacting occur in a fluid catalytic cracking reactor, wherein effluent from the fluid catalytic cracking reactor contains cracked hydrocarbon products, wherein the cracked hydrocarbon products consist of at least one member selected from the group consisting of methane, ethane, ethylene, propylene and LPG ($C_3+C_4$).

12. The method of claim 9, wherein the preheating is conducted in a heat exchanger.

13. The method of claim 9, wherein the gas comprises methane.

* * * * *